United States Patent
Kemp et al.

(10) Patent No.: US 11,903,777 B2
(45) Date of Patent: Feb. 20, 2024

(54) SYSTEMS AND METHODS FOR CLEANING ENDOSCOPIC INSTRUMENTS

(71) Applicant: INTUITIVE SURGICAL OPERATIONS, INC., Sunnyvale, CA (US)

(72) Inventors: Joseph A Kemp, San Jose, CA (US); Federico Barbagli, San Francisco, CA (US); Joseph R. Callol, San Mateo, CA (US); Vincent Duindam, San Francisco, CA (US); Lucas S. Gordon, Mountain View, CA (US); Randall L. Schlesinger, San Mateo, CA (US); Samuel B. Schorr, East Palo Alto, CA (US); Worth B. Walters, Campbell, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 917 days.

(21) Appl. No.: 16/763,171

(22) PCT Filed: Nov. 13, 2018

(86) PCT No.: PCT/US2018/060796
§ 371 (c)(1),
(2) Date: May 11, 2020

(87) PCT Pub. No.: WO2019/099396
PCT Pub. Date: May 23, 2019

(65) Prior Publication Data
US 2020/0383750 A1    Dec. 10, 2020

Related U.S. Application Data

(60) Provisional application No. 62/585,922, filed on Nov. 14, 2017.

(51) Int. Cl.
*A61B 90/70*    (2016.01)
*A61M 25/00*    (2006.01)
(Continued)

(52) U.S. Cl.
CPC ........ *A61B 90/70* (2016.02); *A61B 17/00234* (2013.01); *A61M 25/00* (2013.01);
(Continued)

(58) Field of Classification Search
CPC .............. A61M 5/142; A61M 5/14244; A61M 5/14276; A61M 5/168; A61M 5/16804;
(Continued)

(56) References Cited

U.S. PATENT DOCUMENTS 4,093,545 A  *  6/1978  Cullis ................ A61M 1/1694
                                                        210/136
6,380,732 B1     4/2002  Gilboa
(Continued)

FOREIGN PATENT DOCUMENTS

WO      WO-9528198 A1    10/1995
WO      WO-2016025465 A1  2/2016

OTHER PUBLICATIONS

International Preliminary Report on Patentability for Application No. PCT/US2018/060796, dated May 28, 2020, 9 pages (ISRG10780/PCT).
(Continued)

*Primary Examiner* — Jason E Flick
*Assistant Examiner* — Justin L Zamory
(74) *Attorney, Agent, or Firm* — Haynes & Boone, LLP.

(57)    ABSTRACT

A method for controlling fluid delivery to a medical instrument comprises releasing, from a reservoir of a known size and having fluid at a volume and a first fluid pressure, a released fluid volume of the fluid to the medical instrument. The method also comprises measuring a vented fluid volume
(Continued)

and determining a discharged fluid volume through the medical instrument based on the released fluid volume and the vented fluid volume.

23 Claims, 9 Drawing Sheets

(51) Int. Cl.
*A61M 39/22* (2006.01)
*A61B 17/00* (2006.01)
*G01F 13/00* (2006.01)
*G05D 7/06* (2006.01)
*A61B 34/20* (2016.01)
*A61B 34/37* (2016.01)
*A61B 1/12* (2006.01)
*A61B 1/267* (2006.01)

(52) U.S. Cl.
CPC ........... *A61M 39/223* (2013.01); *G01F 13/00* (2013.01); *G05D 7/0623* (2013.01); *A61B 1/125* (2013.01); *A61B 1/2676* (2013.01); *A61B 34/37* (2016.02); *A61B 2017/00314* (2013.01); *A61B 2017/00323* (2013.01); *A61B 2034/2051* (2016.02); *A61B 2034/2061* (2016.02); *A61B 2090/701* (2016.02); *A61B 2217/005* (2013.01); *A61B 2217/007* (2013.01); *A61M 2025/0019* (2013.01); *A61M 2205/3334* (2013.01); *A61M 2205/50* (2013.01)

(58) Field of Classification Search
CPC .......... A61M 5/16822; A61M 5/16831; A61M 5/16854; A61M 5/16877; A61M 2005/14208; A61M 2025/0019; A61M 39/223; A61M 2205/3334; A61B 90/70; A61B 2090/701; A61B 1/125; G01F 13/00; G05D 7/0623
See application file for complete search history.

(56) References Cited

U.S. PATENT DOCUMENTS

| | | | |
|---|---|---|---|
| 6,389,187 | B1 | 5/2002 | Greenaway et al. |
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 10,039,440 | B2 | 8/2018 | Fenech et al. |
| 10,542,868 | B2 | 1/2020 | Gordon et al. |
| 2005/0126578 | A1 | 6/2005 | Garrison et al. |
| 2006/0013523 | A1 | 1/2006 | Childlers et al. |
| 2009/0260625 | A1 | 10/2009 | Wondka |
| 2009/0306476 | A1* | 12/2009 | Banik ................ A61B 1/00103 600/158 |
| 2010/0076370 | A1 | 3/2010 | Howlett et al. |
| 2012/0282111 | A1 | 11/2012 | Nip et al. |
| 2013/0066297 | A1 | 3/2013 | Shtul et al. |
| 2013/0172805 | A1 | 7/2013 | Truckai et al. |
| 2013/0317292 | A1 | 11/2013 | Shtul |
| 2013/0324928 | A1* | 12/2013 | Kruse ............... A61M 5/16854 604/151 |
| 2017/0238795 | A1 | 8/2017 | Blumenkranz et al. |

OTHER PUBLICATIONS

International Search Report and Written Opinion for Application No. PCT/US2018/060796, dated May 10, 2019, 13 pages (ISRG10780/PCT).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

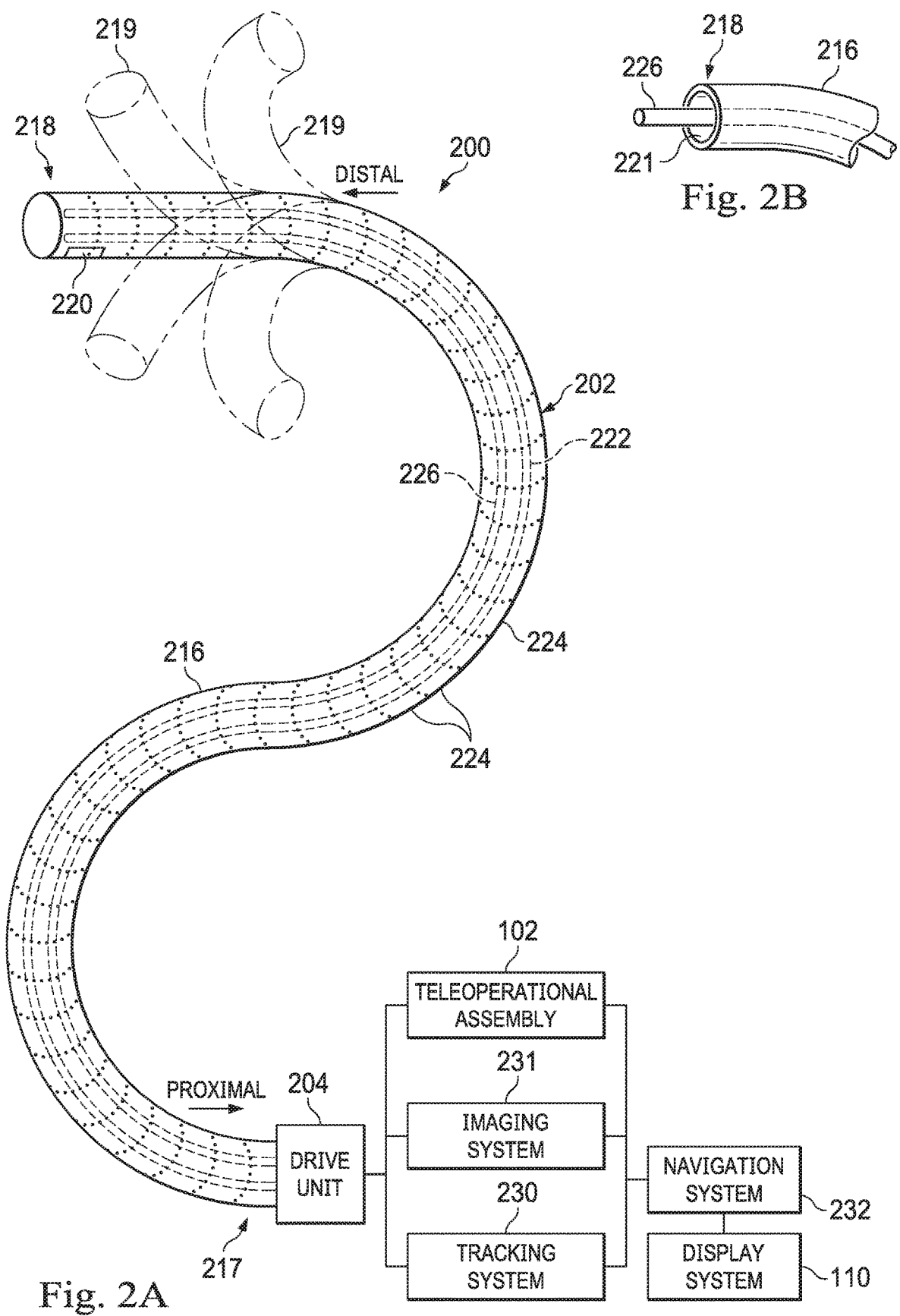

SYSTEMS AND METHODS FOR CLEANING ENDOSCOPIC INSTRUMENTS

CROSS-REFERENCE TO RELATED APPLICATIONS

This patent application is the U.S. national phase of International Application No. PCT/US2018/060796, filed Nov. 13, 2018, which designated the U.S. and claims priority to and the benefit of the filing date of U.S. Provisional Application 62/585,922, filed Nov. 14, 2017, all of which are incorporated by reference in their entirety.

FIELD

The present disclosure is directed to systems and methods for controlling a steerable elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. To provide a clear field of view, the imaging instrument should be free of debris or other view obstructing material. Systems and methods are needs to clean the imaging instruments while the instruments are inserted in the patient anatomy.

SUMMARY

The embodiments of the invention are best summarized by the claims that follow the description.

Consistent with some embodiments, a method for controlling fluid delivery to a catheter comprises charging a reservoir, of a known size, with a fluid to a volume at an initial fluid pressure and releasing a released fluid volume of the fluid from the reservoir to the catheter. The method also comprises measuring a vented fluid volume and determining a discharged fluid volume through the catheter based on the released fluid volume and the vented fluid volume.

Consistent with some embodiments, a system for controlling fluid delivery to a catheter comprises a fluid reservoir of known size charged with a fluid to an initial known fluid volume at an initial fluid pressure and a valve system coupled between the fluid reservoir and the catheter. The system also comprises a vent, a flow sensor coupled between the valve system and the vent, and a control system including one or more processors. The control system is configured to activate the valve system to release a released fluid volume of the fluid from the fluid reservoir to the catheter, measure with the flow sensor a vented fluid volume through the vent, and determine a discharged fluid volume of fluid discharged through the catheter based on the released fluid volume and the vented fluid volume.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 2A is a simplified diagram of a medical instrument system according to some embodiments.

FIG. 2B is a simplified diagram of a medical instrument with an extended medical tool according to some embodiments.

Figure 1:
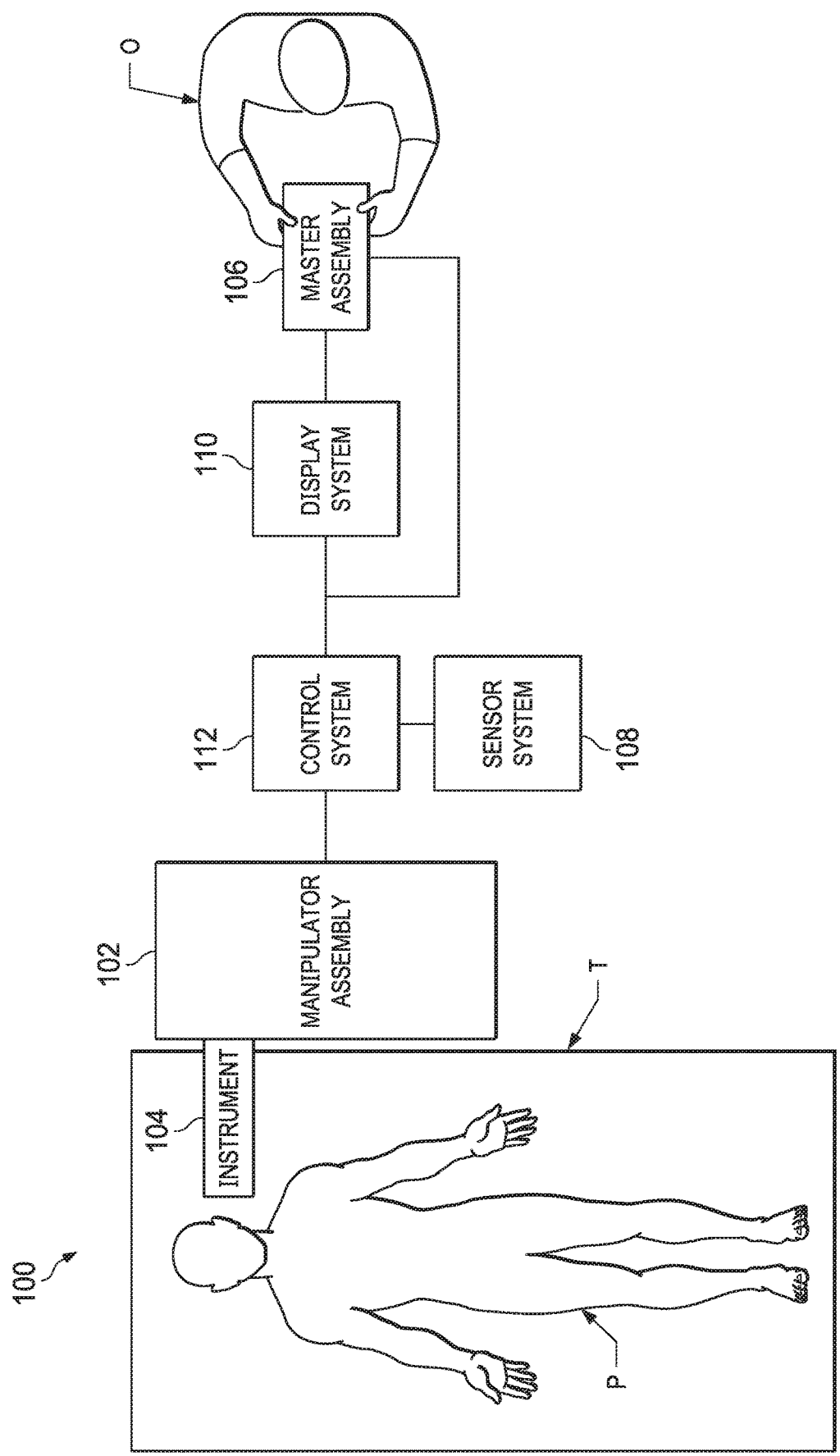
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator O (e.g., a surgeon, a clinician, or a physician as illustrated in FIG. 1) to view the interventional site and to control teleoperational manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or an imaging system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may include components of an imaging system (discussed in more detail below), which may include an imaging scope assembly or imaging instrument that records a concurrent or real-time image of a surgical site and provides the image to the operator or operator O through one or more displays of medical system 100, such as one or more displays of display system 110. The concurrent image may be, for example, a two or three dimensional image captured by an imaging instrument positioned within the surgical site. In some embodiments, the imaging system includes endoscopic imaging instrument components that may be integrally or removably coupled to medical instrument 104. However in some embodiments, a separate endoscope, attached to a separate manipulator assembly may be used with medical instrument 104 to image the surgical site. In some examples, as described in detail below, the imaging instrument alone or in combination with other components of the medical instrument 104 may include one or more mechanisms for cleaning one or more lenses of the imaging instrument when the one or more lenses become partially and/or fully obscured by fluids and/or other materials encountered by the distal end of the imaging instrument. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 filed Aug. 11, 2016 disclosing "Systems and Methods for Cleaning an Endoscopic Instrument"; U.S. patent application Ser. No. 15/508,923 filed Mar. 5, 2017 disclosing "Devices, Systems, and Methods Using Mating Catheter Tips and Tools"; and U.S. patent application Ser. No. 15/503,589 filed Feb. 13, 2017 disclosing "Systems and Methods for Cleaning an Endoscopic Instrument," each of which is incorporated by reference herein in its entirety. The imaging system may be implemented as hardware, firmware, software or a combination thereof which interact with or are otherwise executed by one or more computer processors, which may include the processors of a control system 112.

Display system 110 may also display an image of the surgical site and medical instruments captured by the imaging system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104.

As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an imaging instrument (e.g., an image capture probe) also within flexible body 216. In various embodiments, medical instrument 226 may itself be an imaging instrument (e.g., an image capture probe) that includes a distal portion with a stereoscopic or monoscopic camera at or near distal end 218 of flexible body 216 for capturing images (including video images) that are processed by a imaging system 231 for display and/or provided to tracking system 230 to support tracking of distal end 218 and/or one or more of the segments 224. The imaging instrument may include a cable coupled to the camera for transmitting the captured image data. In some examples, the imaging instrument may be a fiber-optic bundle, such as a fiberscope, that couples to imaging system 231. The imaging instrument may be single or multi-spectral, for example capturing image data in one or more of the visible, infrared, and/or ultraviolet spectrums. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from imaging system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
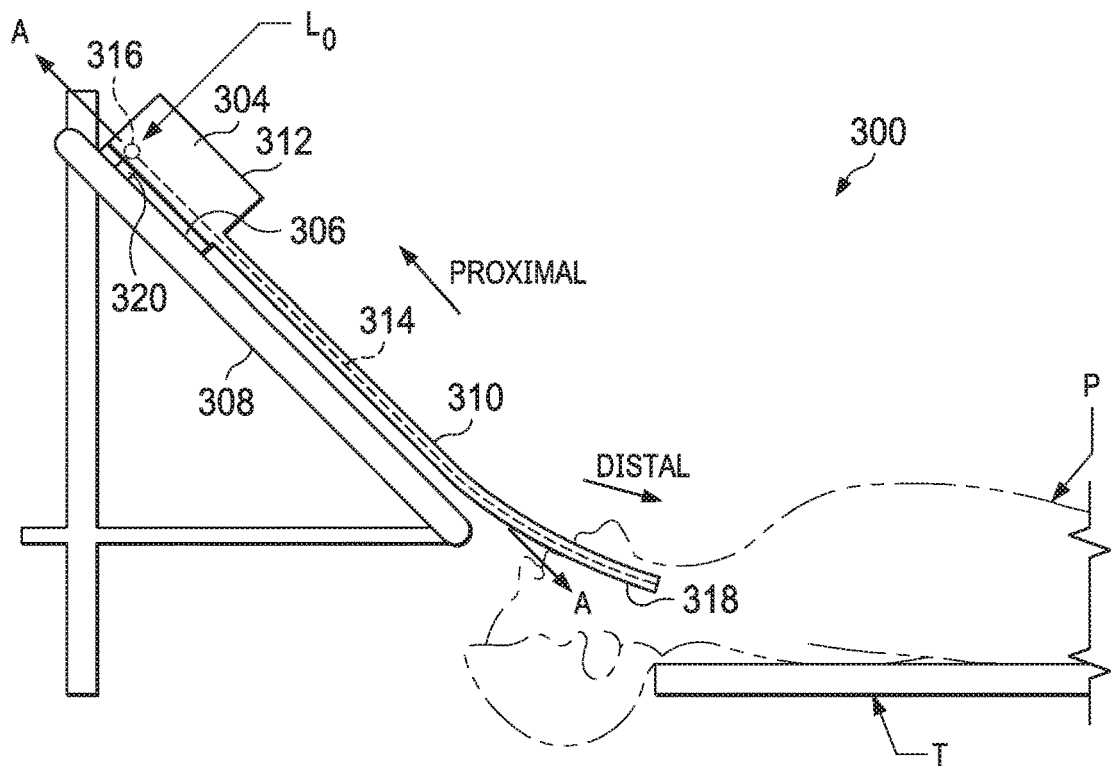
FIGS. 3A and 3B are simplified diagrams of side views of a patient coordinate space including a medical instrument mounted on an insertion assembly according to some embodiments.
Figure 3B:
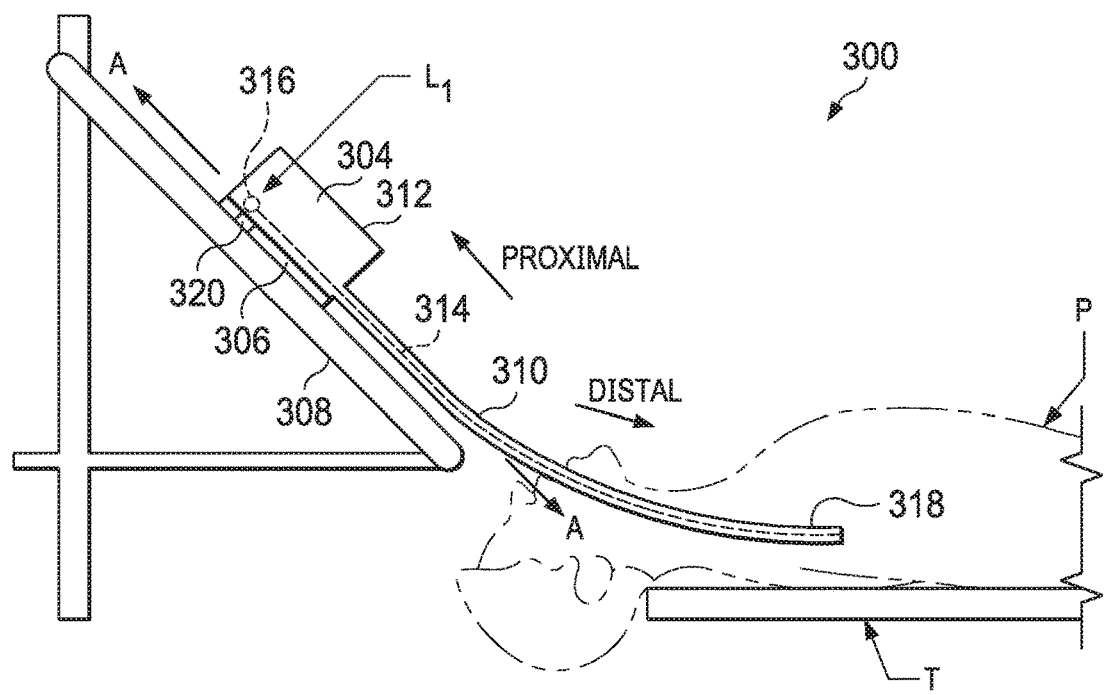

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

Figure 4:
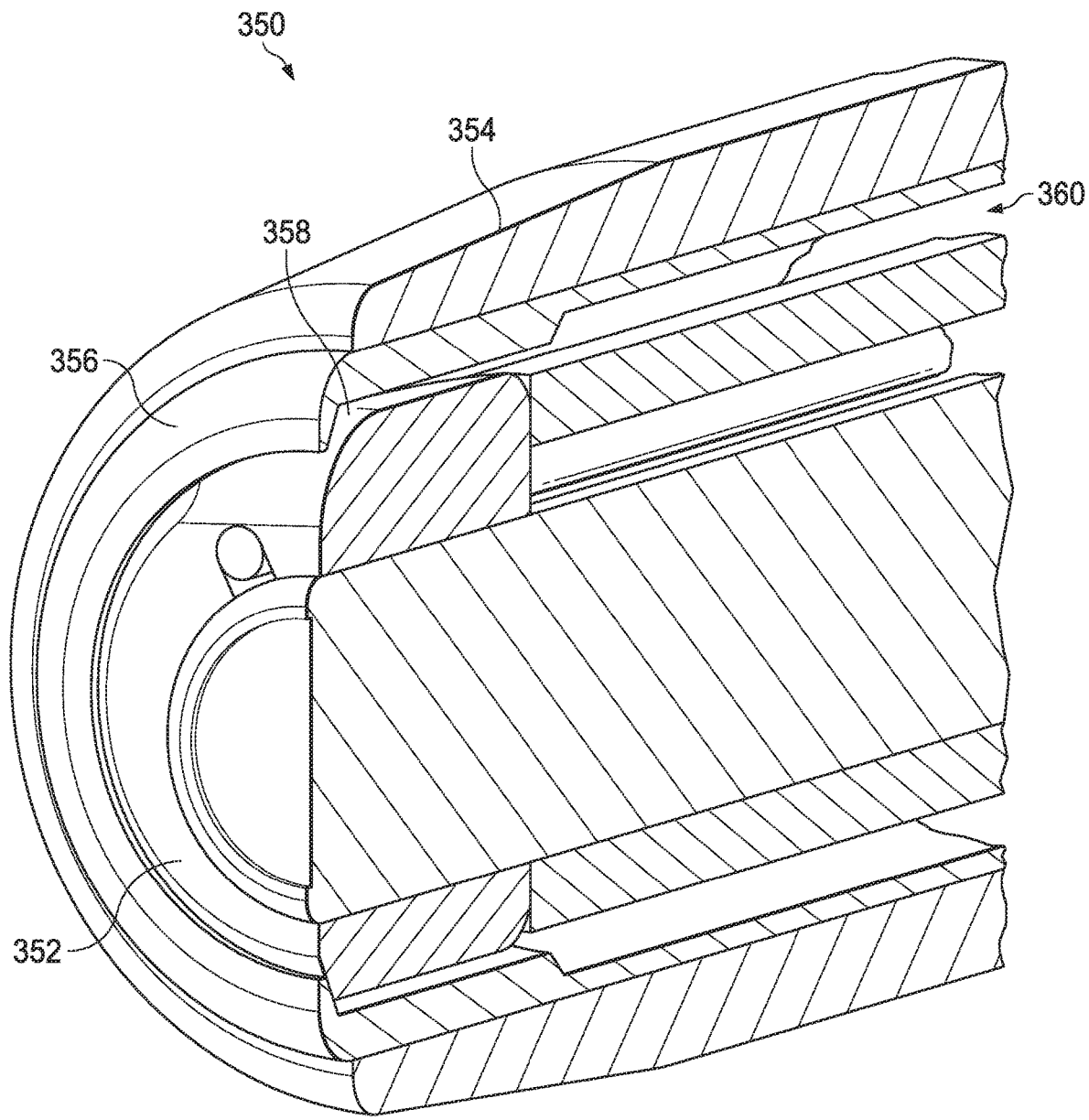
FIG. 4 is a cross-sectional view of a distal end of an imaging instrument seated within a distal end of a catheter such that a fluid dispensing path is formed.

FIG. 4 is an isometric cross-sectional view of a distal portion of a medical instrument system 350 (e.g., the medical instrument system 200) including an imaging instrument 352 (e.g., the medical instrument 226) positioned within a lumen of a catheter 354 (e.g., elongate device 202) where a distal end of the imaging instrument 352 is seated within the distal portion of the catheter 354. In a fully seated configuration, the distal end of the imaging instrument 352 abuts the distal tip 356 of the catheter 354 to provide at least a partial seal that limits the ingress of fluid and tissue into the catheter 354. In some examples, the imaging instrument 352 can be seated in a configuration where the distal end of the imaging instrument 352 is spaced a small distance proximal to the distal tip 356 of the catheter 354. The spacing can help form a well acting as the partial seal. The distal tip of catheter 354 and/or the distal end of the imaging instrument 352 may be shaped to provide an orifice such as a slot, notch, opening, or passage 358 that allows fluid to be discharged from a flow path 360 between a surface of the lumen of the catheter and an outer surface of the imaging instrument to an area distal of the imaging instrument. The orifice 358 may vary in shape, size, and/or number such that multiple orifices increases the volume of fluid delivered and the amount of fluid engagement with contaminants. The orientation of the multiple orifices can be optimized radially and circumferentially to provide effective cleaning based on fluid volume, for example, the multiple orifices may be spaced circumferentially to form a complete concentric gap between the catheter distal tip 356 and the imaging instrument 352. This medical instrument is described in greater detail in U.S. patent application Ser. No. 15/508,923 filed Mar. 5, 2017 disclosing "Devices, Systems, and Methods Using Mating Catheter Tips and Tools" which is incorporated by reference herein in its entirety.

The passage 358 of medical instrument system 350 may be used to provide a cleaning fluid including liquids or gases such as saline, water, carbon dioxide, oxygen, nitrogen, air, or a combination of gas and liquid (e.g. saline and air) in a mist form across the distal end of the imaging instrument to dislodge debris from a lens of the imaging instrument and remove obstructions to the field of view. In other embodiments, the fluid may be conveyed to the distal tip of the imaging instrument through, for example, vents, dedicated conduits in the medical instrument or vision systems, other instruments in the surgical workspace, or other discharging orifice configurations created by the mating of the instrument and catheter. Because the conveyed cleaning fluid is discharged into the patient anatomy, the discharged fluid volume, pressure, and/or flow rate may be limited to prevent injury to the patient anatomy. For example, if the medical instrument system is used in lung airways, the volume, pressure, and/or flow rate of discharged fluid may be limited to avoid rupturing the airway in which the instrument is located or to prevent pneumothorax. The number of fluid discharges, the duration of each discharge, the velocity of each discharge, the compressibility of the fluid discharged, the volume of the fluid path from the source to the discharging tip, and the size of the discharging orifice are all examples of variables which may contribute to the volume of discharged fluid. When the fluid is discharged through the flow path 360 and the passage 358 of the medical instrument system 350 as shown in FIG. 4, a predictable discharge volume may be predicated on a proper seating of the distal end of the imaging instrument within the distal tip of the catheter. When the imaging instrument is properly seated in the catheter such that a seal is formed around the distal tip of the imaging instrument and catheter allowing cleaning fluid to be conveyed only through the passage 358, the discharge volume may be controlled and predictable. When the imaging instrument is not sealed within the distal tip of the catheter and cleaning fluid is able to leak into the patient anatomy around a circumference of the distal end of the medical instrument, the discharge volume may be inconsistent and unpredictable. A predictable flow configuration, with the imaging instrument properly seated in the catheter, is useful to avoid releasing a damaging amount a fluid that could injure a patient. While a seated and sealed imaging instrument is beneficial for the predictable discharge of cleaning fluid, the medical instrument system may also be configured to permit pullback of the imaging instrument from the sealed and seated position to determine if the catheter tip is facing an anatomical wall or is clogged with debris. A positive seating mechanism, such as a spring-based mechanism, may apply a force to bias the imaging instrument toward a seated and sealed configuration but that force may be overcome by user intervention to allow the imaging instrument to be pulled back, away from the tip of the catheter.

In various embodiments, for example in the lung anatomy, the position and/or orientation of the distal tip of the catheter relative to an airway wall may be known (e.g., from registration to a pre-operative anatomic model or from imaging performed during a procedure) or sensed (e.g., based on a force sensor) to determine if the distal tip is against an airway wall. If the distal tip is against the airway wall or a threshold distance from the airway wall, an action may be implemented to prevent pneumatocele or a pneumothorax. For example, an alert may be provided to the operator, fluid discharge may be disallowed, a different compressibility (e.g., a mist or liquid may be delivered instead of a gas) may be delivered, the velocity of fluid discharge may be altered, or a lower volume of fluid may be discharged based on the known or sensed position or orientation. The lower volume can scale based on measured or calculated distance from the airway wall.

Figure 5:
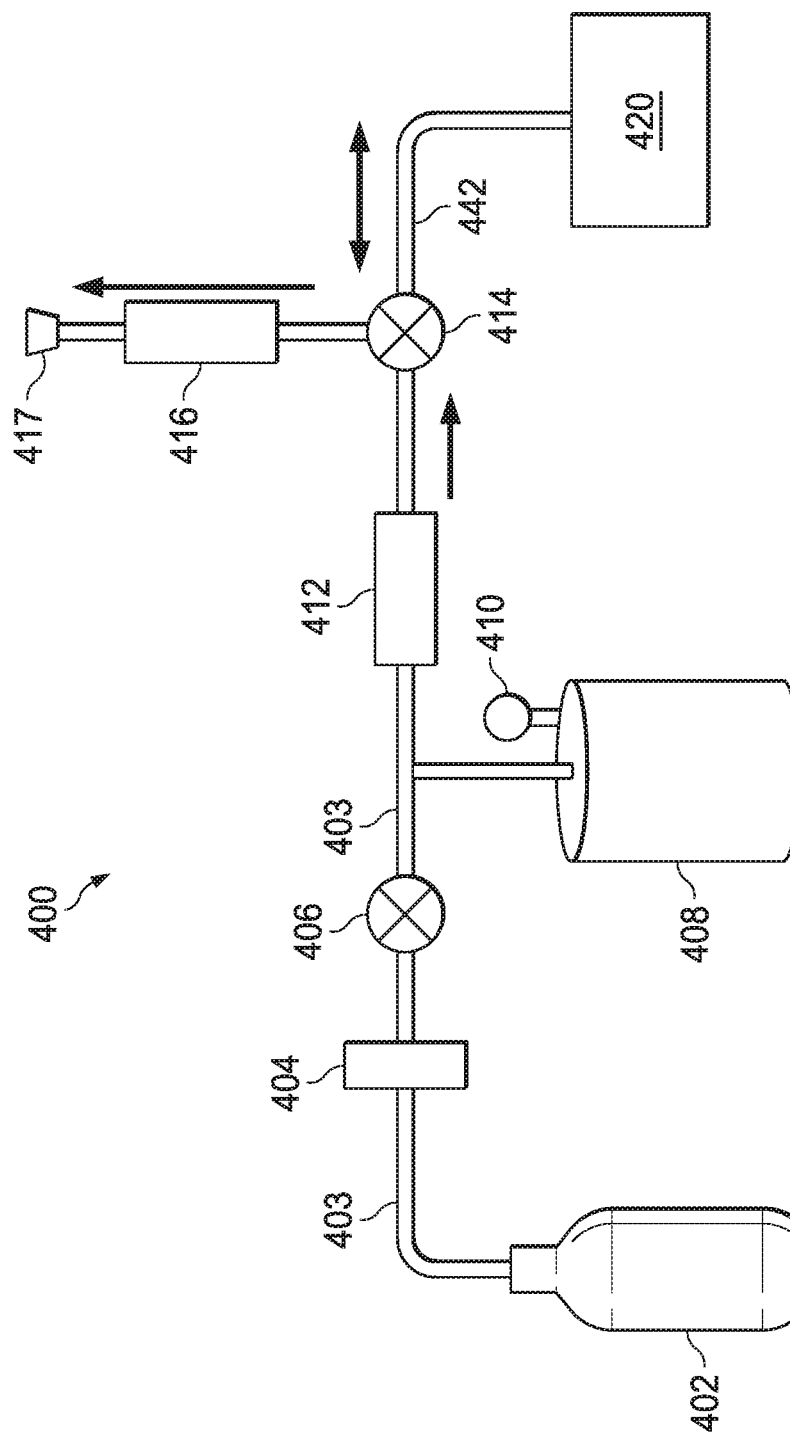
FIG. 5 illustrates a fluid delivery system according to some embodiments.

FIG. 5 illustrates a fluid delivery system 400 that may be used for a variety of purposes including delivering a predictable fluid discharge, evaluating the resistance to flow in a medical instrument system, and calibrating a fluid discharge. The system 400 includes a fluid source 402, a regulator 404, a valve system 406, a fluid reservoir 408, a pressure sensor 410, a flow restrictor 412, a valve system 414, a flow sensor 416, and a vent 417. The flow sensor may include a flow meter, a pitot tube, or an equivalent sensor. The components of the fluid delivery system may be coupled by tubing 403 or other conduit material. One or more of the components of fluid delivery system 400 may be omitted. In alternative embodiments, the valve system 414 may include more than one valve with each valve opened and closed independently or in unison to provide the quick response needed to achieve precise discharge durations and velocities.

Figure 6:
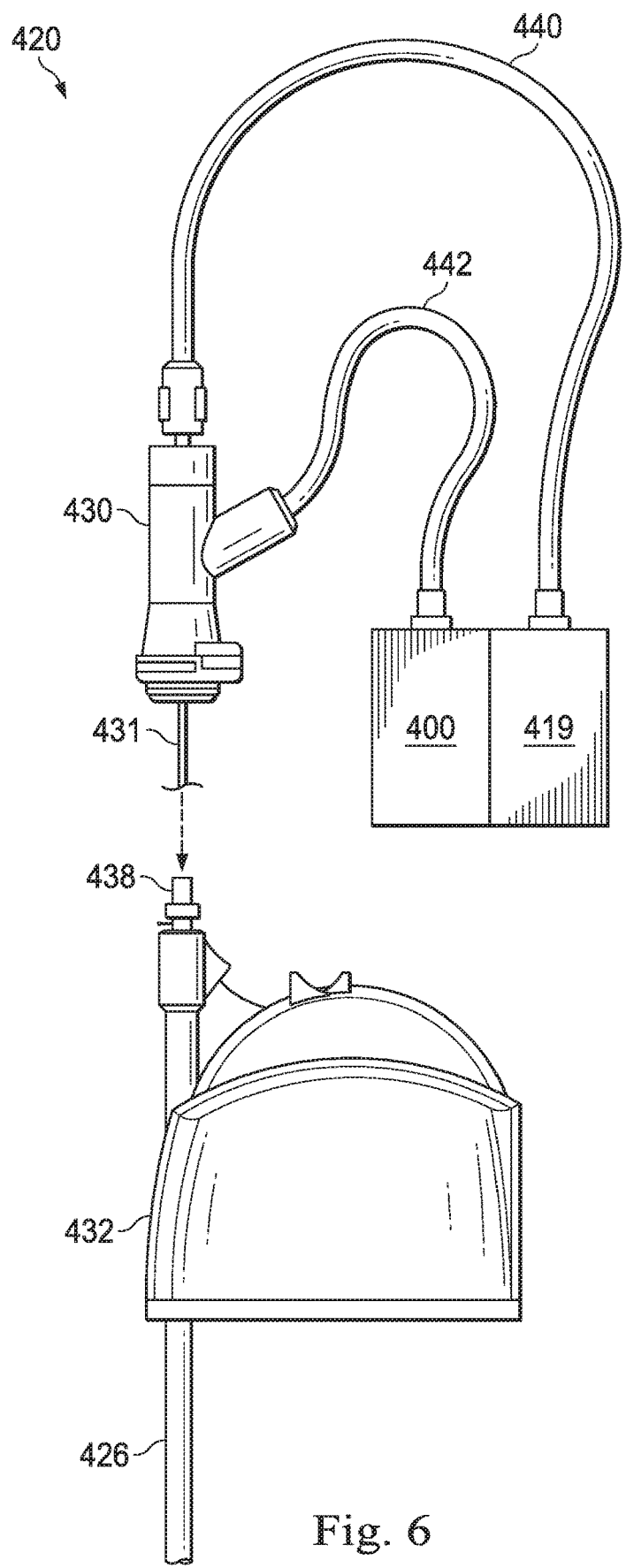
FIG. 6 illustrates a medical instrument system according to some embodiments.

The fluid delivery system 400 may be coupled to a medical instrument system 420 (e.g., instrument system 104) via conduit 442 which conveys fluid from the fluid delivery system 400 to the medical instrument system 420. As illustrated in FIG. 6, the medical instrument system 420 includes an elongate flexible guide instrument or catheter 426 (e.g. catheter 216, 354) through which an imaging instrument 431 (e.g. imaging instrument 352) extends.

An imaging system 419 (e.g. imaging system 231) may be coupled to the imaging instrument 431 via cabling 440 and an instrument coupler 430. When the imaging instrument 431 is extended through the elongate flexible guide instrument 426, the imaging coupler 430 is coupled to a catheter port 438. A catheter housing 432 is coupled to a proximal end of the elongate flexible guide instrument 426. The imaging instrument extending in the elongate flexible guide instrument 426 may be communicatively coupled to processors of the imaging system 419 by the cabling 440 that conveys power, image data, instruction signals or the like. The imaging coupler 430 also couples the fluid delivery system 400 to the proximal end of the elongate flexible guide instrument 426 through coupler 430 and catheter port 438.

Figure 11:
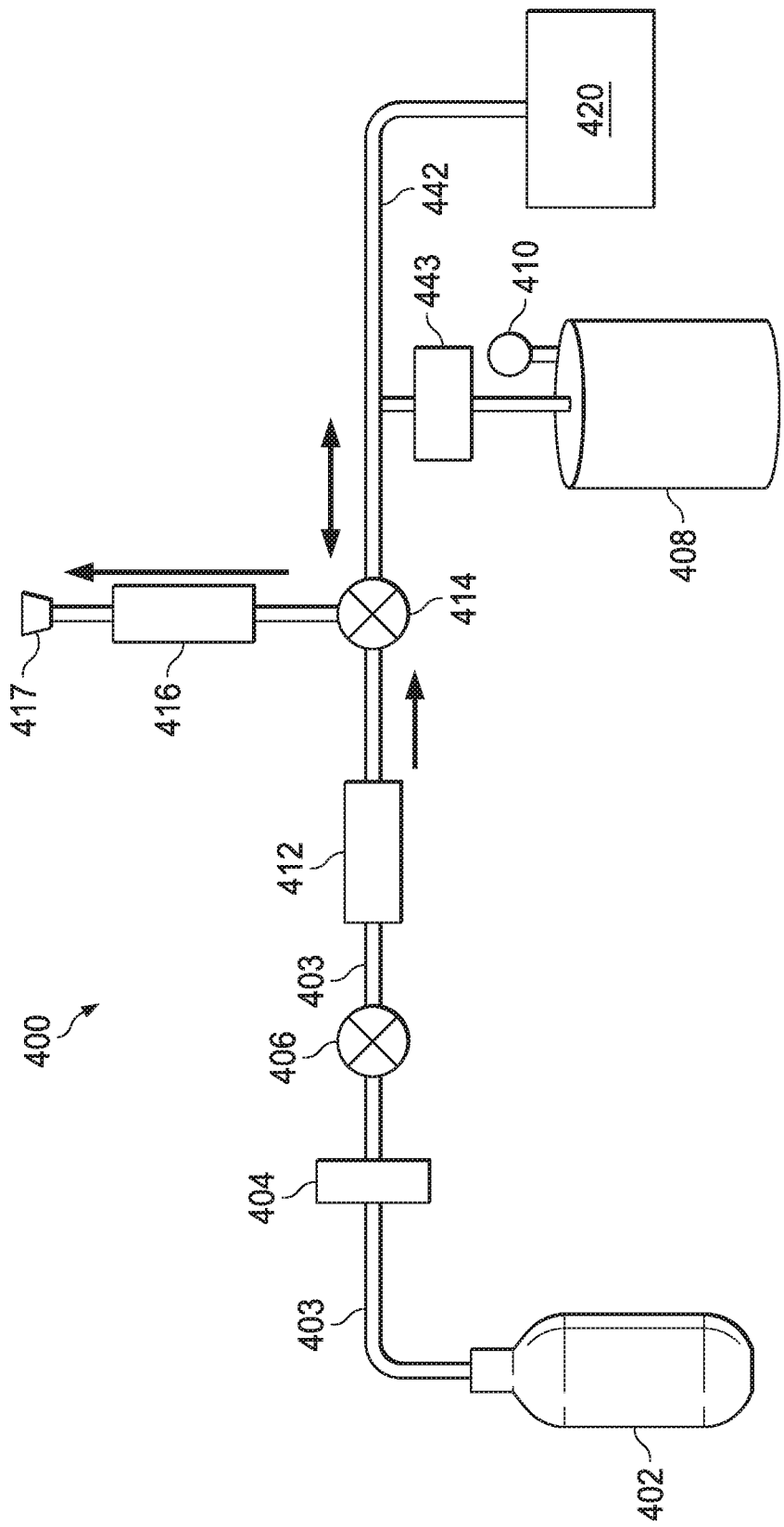
FIG. 11 illustrates a fluid delivery system according to some embodiments.

The fluid delivery system 400 could be used to deliver liquid, gas, or a combination of liquid and gas. In an alternative embodiment shown in FIG. 11, the fluid delivery system 400 could further include a pneumatic cuff system 443 to control the distribution of the liquid. In the embodiment of FIG. 11, the reservoir 408 is located between valve 414 and the medical instrument system 420. The pneumatic cuff system 443 includes a pneumatic cuff membrane inserted in the reservoir 408 such that air pressure applied to the pneumatic cuff system 443 from the side of the valve 414, in the energized state, causes the fluid inside of the reservoir 408 to be pushed out to conduit 442 to be delivered to the medical instrument system 420. In this embodiment, when valve 414 is deactivated excess pneumatic cuff pressure would be released via flow sensor 416, and the fluid flow through conduit 442 to medical instrument 420 would cease. With this method of delivery, distributed fluid may be measured using measured differential pressure over a known restrictor 412 and time. These measurements may be used to calculate flow rate and volume released to the pneumatic cuff system 443. Using the flow rate and volume measurements along with pressure inside of the pneumatic cuff it may be possible to approximate the displaced fluid volume in the reservoir. Additionally, the displaced volume may be calculated using the flow meter upon release of excess gas in the pneumatic cuff after an energization cycle. In an alternative embodiment, a combination of liquid and gas could be delivered using fluid delivery system 400 to deliver gas and delivering liquid using a syringe (not shown) coupled to the instrument coupler 430. In one example, the gas and liquid could be simultaneously delivered in a mist form. In another example, gas and liquid delivery can occur independently in an alternating manner.

One or more calibration techniques for calibration of the fluid discharge may be used to improve accuracy and consistency. One factor used in calibrating discharge may be actuation timing. For example, at delivery valve open times ranging from 3 ms to 60 ms, a ratio between pressure drop computed volume discharge and vent measured volume discharge may be recorded. The ratios may be used to provide a multiplier for the flow meter readings. Another factor in calibrating discharge may be no-flow offset. The type of fluid discharged may impact a raw offset signal count of the flow meter during no flow conditions. Offset compensations may be determined for different types of media, including carbon dioxide and air. Another factor in calibrating discharge is idle time is idle time variation. The puff volume may generally err high following periods of system idle time. Thus, measurements may be compensated based on prior system idle time.

Figure 7:
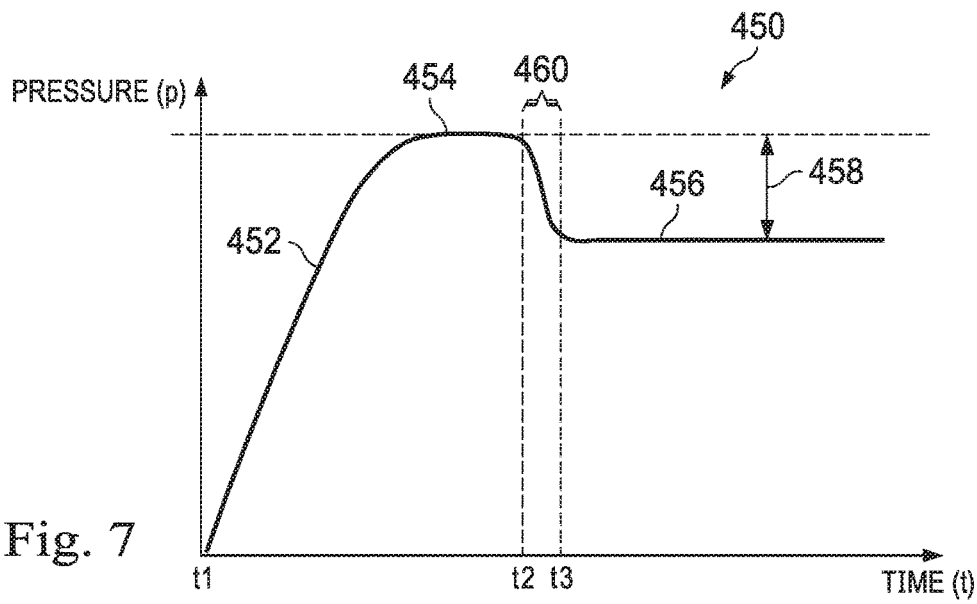
FIG. 7 is a graph illustrating pressure change in a fluid reservoir of the fluid delivery system of FIG. 5.
Figure 8:
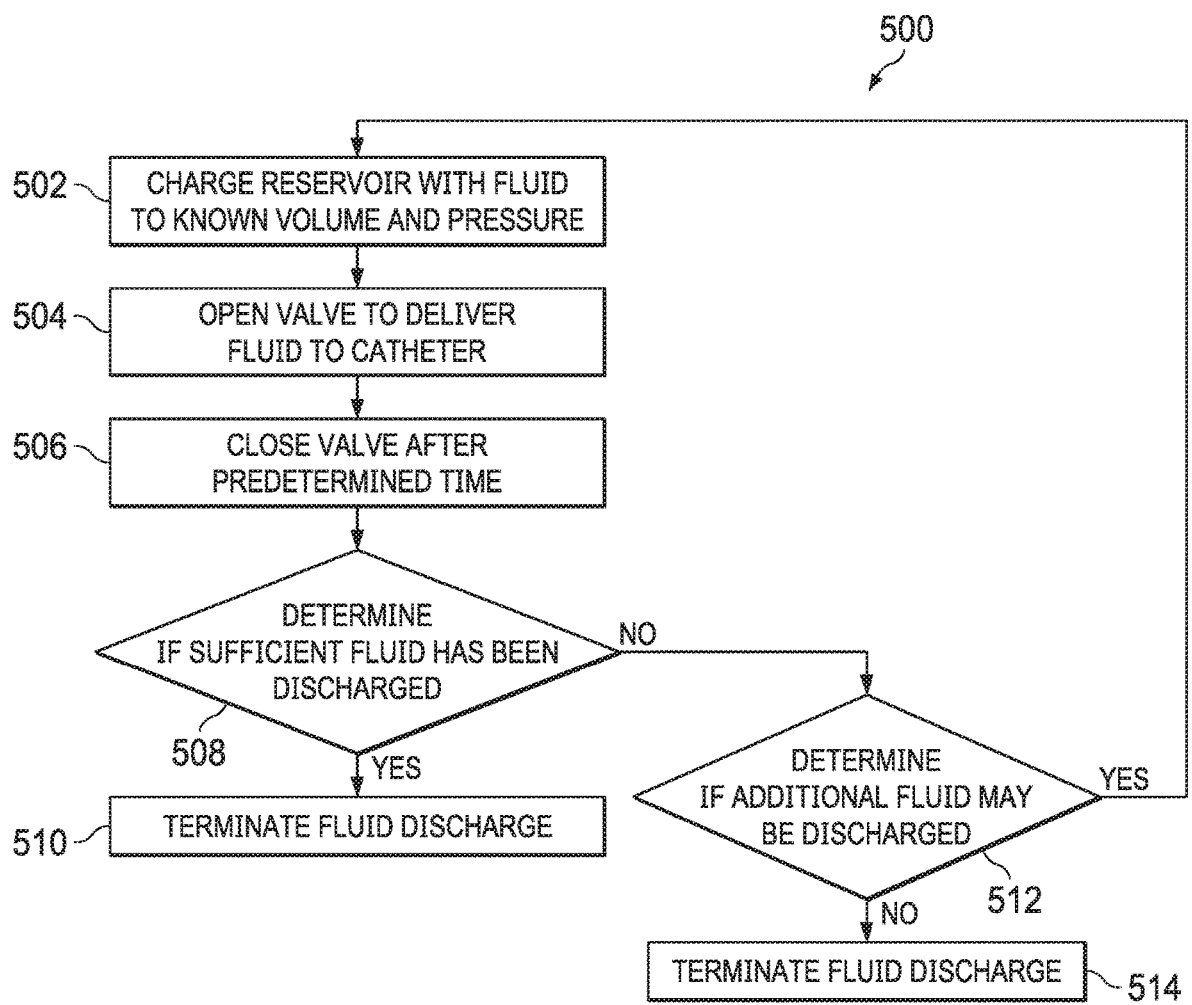
FIG. 8 illustrates a method of controlling fluid delivery to a medical instrument.

FIG. 7 illustrates a method 500 of using components of the fluid delivery system 400 to provide a controlled fluid delivery to the medical instrument system 420 to clean a distal end of the imaging instrument. The method 500 is illustrated in FIG. 8 as a set of operations or processes. Not all of the illustrated processes may be performed in all embodiments of method 500. Additionally, one or more processes that are not expressly illustrated in FIG. 8 may be included before, after, in between, or as part of the illustrated processes. In some embodiments, one or more of the processes of method 500 may be implemented, at least in part, in the form of executable code stored on non-transitory, tangible, machine-readable media that when run by one or more processors (e.g., the processors of control system 112) may cause the one or more processors to perform one or more of the processes.

At a process 502, the reservoir 408, which has a known size and container volume, is charged to a known or measurable volume and/or pressure. More specifically, the valve system 406 may be actuated to an open position to allow fluid to flow from the fluid source 402 to the reservoir 408. In various embodiments, the fluid source may be a tank holding fluid such as saline, carbon dioxide, oxygen, nitrogen, water, compressed air, or a combination of fluids such as saline and carbon dioxide or saline and compressed air. For example, the fluid source may be a high pressure air tank stationed on a movable cart in the surgical environment. The air pressure in the air tank may be, for example, approximately 2000 psi. A regulator 404 may regulate the pressure of the fluid passing through the valve system 406 to a working pressure. For example, the regulator may regulate the pressure of air flowing from a high pressure air tank to a working pressure of between approximately 10-150 psi. In one example, the regulated pressure may be 145 psi. The pressure sensor 410 may provide a reading of the pressure in the reservoir 408 of known size allowing for a calculation of the volume of fluid at atmospheric pressure.

At a process 504, the valve system 414 is actuated to an open position to allow fluid flow from the reservoir 408 to the medical instrument system 420. At a process 506, the valve system 414 is actuated a closed position after a predetermined time to terminate fluid flow from the reservoir 408 to the medical instrument system 420 and allow flow from medical instrument 420 to flow sensor 416 and vent 417. As a safety precaution, the optimal volume, pressure, and/or flow rate at the distal tip of the catheter 426 may be limited based on factors including, but not limited to the size of the anatomic passageway in which the catheter 426 is inserted, the patient's health, and the location in the patient anatomy (e.g., proximity to the lung pleura). As a safety precaution, the volume of fluid discharged (between processes 504 and 506) over a short predetermined period of time (e.g. approximately 5-100 milliseconds) may be limited to prevent patient injury. The number of fluid discharges and the duration of each discharge may be calibrated and controlled to limit the overall maximum fluid discharge. In various embodiments in a human lung, for example, an overall maximum fluid volume of approximately 10 cc may be discharged through a series of small fluid discharges but the maximum may depend on fluid type and rate of discharge. In various embodiments, the target volume for each discharge (e.g. a single air puff) may be 1-2 cc. Thus 2-3 discharges of a 1 cc volume may be permissible before the overall maximum fluid volume of 10 cc has been discharged.

At a process 508, a determination is made as to whether sufficient fluid has been discharged through the distal end of the catheter 426 of medical instrument system 420. This determination may be based, for example, on whether a predetermined number of discharges of a predetermined volume have occurred, on whether an operator determines that obstructions have been cleared from the field of view, or on whether image processing analysis determines that obstructions have been cleared from the field of view. Examples of image processing analysis are discussed in more detail in U.S. patent application Ser. No. 15/503,589 filed Feb. 13, 2017 disclosing "Systems and Methods for Cleaning an Endoscopic Instrument" and U.S. patent application Ser. No. 13/911,705 filed Jun. 6, 2013 disclosing "Systems and Methods for Cleaning a Minimally Invasive Instrument," each of which is incorporated by reference herein in its entirety.

At a process 510, if sufficient fluid has been discharged, further discharge is terminated. At a process 512, if sufficient fluid has not been discharged through the distal end of the catheter 426 of medical instrument system 420, a determination is made as to whether additional fluid discharge is permissible. At a process 514, if additional fluid discharge is impermissible, the catheter may be retracted or otherwise repositioned before reattempting a catheter cleaning procedure. In another embodiment, further discharge may be terminated for an extended period (for example 30 seconds). If additional fluid discharge is permissible, the procedure 500 may be repeated beginning at process 502.

Figure 9:
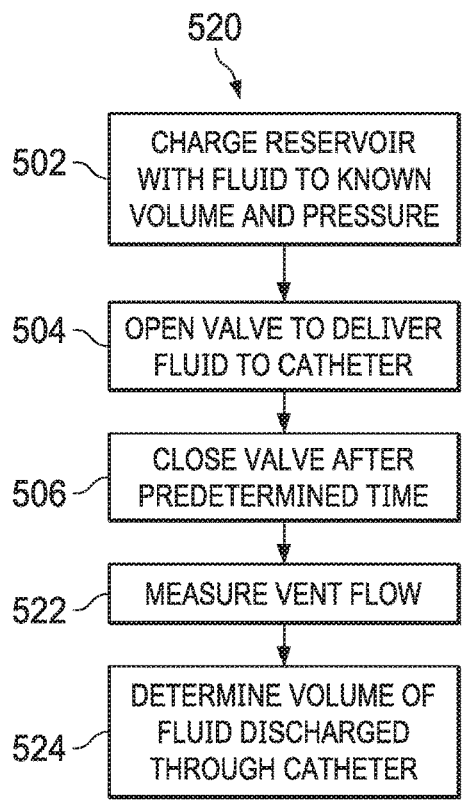
FIG. 9 illustrates a method of tracking the volume of fluid discharge.

FIG. 9 illustrates a method 520 of tracking the discharged fluid volume from the medical instrument system 420 using the flow sensor 416. The method 520 is illustrated in FIG. 9 as a set of operations or processes. Not all of the illustrated processes may be performed in all embodiments of method 520. Additionally, one or more processes that are not expressly illustrated in FIG. 9 may be included before, after, in between, or as part of the illustrated processes. In some embodiments, one or more of the processes of method 520 may be implemented, at least in part, in the form of executable code stored on non-transitory, tangible, machine-readable media that when run by one or more processors (e.g., the processors of control system 112) may cause the one or more processors to perform one or more of the processes.

At a process 502, the reservoir 408 is charged to a known or measurable volume and/or pressure, as previously described. At a process 504, the valve system 414 is actuated to an open position to allow fluid flow from the reservoir 408 to the medical instrument system 420, as previously described. At a process 506, the valve system 414 is actuated to a closed position after a predetermined time to terminate fluid flow from the reservoir 408 to the medical instrument system 420, as previously described. The valve system 414 may include a valve system that has two flow patterns. When actuated to an open position, a first flow pattern of the valve or valve system permits fluid to flow from the reservoir 408 to the medical instrument system 420 while a second flow pattern permits fluid from the medical instrument system 420 to flow through flow sensor 416 and vent to the atmosphere through vent 417. Thus, any excess fluid in the medical instrument may be measured and evacuated through the vent 417.

At a process 522, the vented fluid volume released through the vent 417 may be measured by the flow sensor 416. At a process 524, the volume of fluid discharged through the distal end of the catheter 426 of medical instrument system 420 (and thus, effectively, into the patient anatomy) is determined.

More specifically, the discharged fluid volume from the distal end of the catheter 426 of medical instrument system 420 may be determined through comparison of the vented fluid volume measured at the flow sensor 416 to the known volume and/or pressure in the reservoir 408 prior to opening the valve system 414, and from the measured pressure in the reservoir 408 after closing the valve system 414. FIG. 7 is a graph 450 illustrating the pressure change in the fluid reservoir 408 of the fluid delivery system 400. At time t1, the valve system 406 is actuated to charge the reservoir 408 to a measureable, and therefore known, volume and/or pressure. In various embodiments, a pressure of approximately 145 psi may be maintained in the charged reservoir. After the reservoir 408 is charged, the initial fluid pressure in the reservoir is maintained until the valve system 414 is actuated at time t2. The valve system 414 may be actuated for a precise duration of time 460 which is calibrated to correspond with an expected discharge rate, pressure, and/or volume from the medical instrument system 420. The calibrated time may be based on the expectation that the medical instrument system 420 has a consistent/repeatable flow configuration with the imaging instrument sealed against the catheter 426 such that fluid is allowed to flow only through the cleaning slot. At time t3, the valve system 414 is actuated such that fluid flow from reservoir 408 to instrument system 420 is ceased. In another embodiment, the pressure in the reservoir may be monitored while the valve system 414 is opened, and the valve system 414 may be closed as soon as the measured pressure falls below a predetermined threshold. The pressure in the reservoir 408 after the fluid is released may be measured as the final reservoir pressure (e.g., by the pressure sensor 410), and therefore the pressure drop 458 may be determined. The released fluid volume from the reservoir 408 may not be entirely discharged through the medical instrument system 420 because a portion of the fluid may be vented through the vent 417. At the process 524 in FIG. 8, the discharged volume of fluid through the distal end of the catheter 426 of medical instrument system 420 may be determined as the difference between the released volume of fluid from the reservoir 408 and the vented volume of fluid through the vent 417, as measured by the flow sensor 416. In various embodiments, a pressure sensor may be used as an alternative to a flow sensor. The released volume of fluid from the reservoir 408 may be determined as:

released volume=((the initial reservoir pressure)−(the final reservoir pressure))×(the reservoir volume)/(the atmospheric pressure).

Optionally, the calculated discharged fluid volume may be compared to a threshold safe discharge volume. The threshold safe discharge volume may be the maximum safe volume of fluid that may be discharged into the patient anatomy without causing over-inflation of the anatomic passageway, pneumothorax, pneumatoceles, or other damage to the patient anatomy. Optionally, if the threshold safe discharge volume is exceeded, a warning indicator may be issued to the operator or the control system may provide a delay before allowing a subsequent discharge of fluid. A measured discharge volume that exceeds the threshold may be an indication of an inconsistent or unpredictable flow possibly caused by a mis-seated imaging instrument in the catheter, or other factors. Other factors include, but are not limited to: leaking anywhere distal of valve 406 in the air system 400 or in the instrument system 420, contamination of the fluid flow channel 360 by patient or other fluids, damage to either the catheter instrument or vision instrument causing kinking or blockage of the fluid flow channel 360

In methods 500 and 520, an optional flow restrictor 412 positioned between the reservoir 408 and the medical instrument system 420 may be used to prevent the leak of a large amount of fluid (exceeding the threshold safe discharge) from discharging from the medical instrument system 420. In some embodiments the restrictor may be a glass capillary tube that restricts the flow by approximately 50%. With an adequately sized flow restrictor positioned in the fluid flow path, even a gap created by a mis-seated imaging instrument will not allow the discharge of a fluid volume that exceeds the threshold safe discharge within the allowed activation time of valve 414. The optional flow restrictor may also help to reduce overall volumes used and may allow for easier measurement of dispensed volumes by controlling flow rates.

Figure 10:
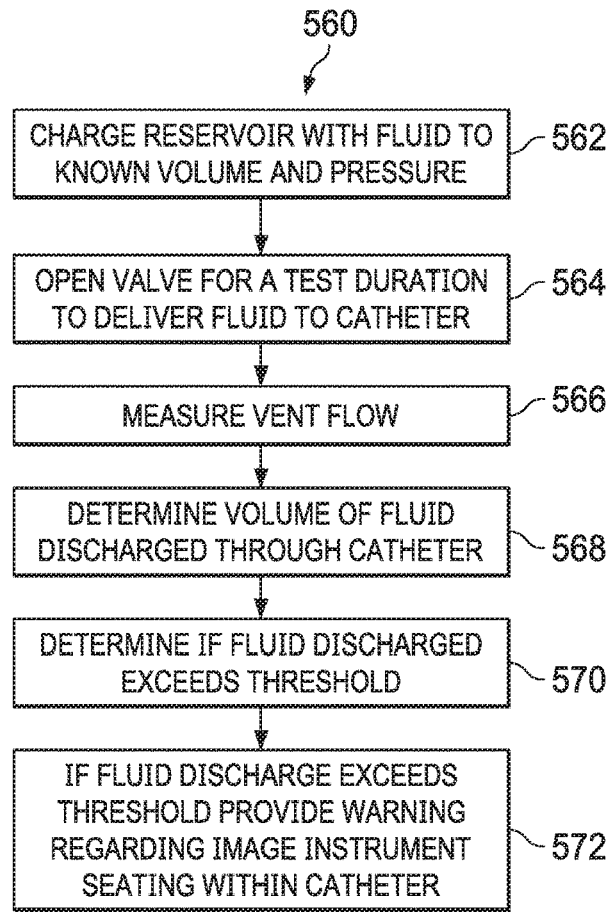
FIG. 10 illustrates a method of evaluating the seating of an imaging instrument within an elongate flexible guide instrument.

FIG. 10 illustrates a method 560 of evaluating the flow resistance in the medical instrument system 420. The method 560 is illustrated in FIG. 10 as a set of operations or processes. Not all of the illustrated processes may be performed in all embodiments of method 560. Additionally, one or more processes that are not expressly illustrated in FIG. 10 may be included before, after, in between, or as part of the illustrated processes. In some embodiments, one or more of the processes of method 560 may be implemented, at least in part, in the form of executable code stored on non-transitory, tangible, machine-readable media that when run by one or more processors (e.g., the processors of control system 112) may cause the one or more processors to perform one or more of the processes.

The medical instrument system 420 is optimally operated at a repeatable flow resistance when the imaging instrument is properly seated and sealed within the catheter. If the evaluation of method 560 determines that the flow resistance exceeds or falls short of a predetermined threshold for flow resistance, a mis-seated or mis-sealed imaging instrument to catheter may be indicated.

At a process 562, the reservoir 408 is charged to a known or measurable volume and pressure, as previously described. At a process 564, the valve system 414 is actuated to an open position to allow fluid flow from the reservoir 408 to the medical instrument system 420 for a short test duration that releases a test fluid volume to the medical instrument system 420. The test duration may be selected to ensure that no more than a safe discharge volume (e.g. 1 cc of fluid) is released from the reservoir even at minimum flow resistance. In one example the test duration may be 5-10 milliseconds. In one example the test duration may be about 7 milliseconds based on the valve's minimum activation time. The time may be longer than 10 milliseconds depending on the size of the restrictor chosen and the amount of resistance generated by the orifice 358. Released volumes may be, for example, between 0.25 and 1.5 cc. In some embodiments, the resistance and activation timing may be calibrated to limit volumes to less than 1.5-2 cc.

At a process 566, the vented fluid volume released through the vent 417 may be measured by the flow sensor 416, as described for process 522. At a process 568, the volume of fluid discharged through the medical instrument system 420 (and thus, effectively, into the patient anatomy) is determined, as described for process 524. At a process 570, the control system determines if the discharged fluid volume exceeds an expected threshold of between 0.25 cc and 0.7 cc associated with a properly seated imaging instrument in the catheter. At a process 572, if the fluid discharge volume exceeds or falls short of the expected threshold, the control system provides a warning indicating that the imaging instrument should be reseated in the catheter. The evaluation method 560 may be repeated until the discharged fluid volume does not exceed the expected threshold.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method for controlling fluid delivery to a medical instrument, the method comprising:
   releasing, from a reservoir of a known size and having fluid at a volume and a first fluid pressure, a released fluid volume of the fluid to the medical instrument;
   measuring a vented fluid volume; and
   determining a discharged fluid volume through the medical instrument based on the released fluid volume and the vented fluid volume.

2. The method of claim 1 wherein the discharged fluid volume is at atmospheric pressure.

3. The method of claim 1 wherein releasing the released fluid volume of the fluid from the reservoir to the medical instrument includes activating a valve for a duration of time calibrated to correspond with an expected discharge volume.

4. The method of claim 1 wherein releasing the released fluid volume of the fluid from the reservoir to the medical instrument includes activating a valve through which passes the released fluid volume.

5. The method of claim 4 wherein the vented fluid volume passes through the valve.

6. The method of claim 1 wherein releasing the released fluid volume of the fluid from the reservoir to the medical instrument includes passing the fluid through a flow restrictor.

7. The method of claim 1 further comprising:
   determining the released fluid volume from the reservoir based on the first fluid pressure and a second fluid pressure in the reservoir after the released fluid volume is released.

8. The method of claim 1 further comprising:
   determining if the discharged fluid volume exceeds a threshold.

9. The method of claim 8 further comprising:
   based on determining that the discharged fluid volume exceeds the threshold, providing a warning indicator.

10. The method of claim 8 further comprising:
    based on determining that the discharged fluid volume exceeds the threshold, preventing release of additional fluid volume from the reservoir.

11. The method of claim 8 further comprising:
    responsive to a determination that an instrument has been moved in the medical instrument after release of the released fluid volume, releasing a second released fluid volume and determining a second discharged fluid volume.

12. A system for controlling fluid delivery to a medical instrument, the system comprising:
    a fluid reservoir of known size having a fluid at a first fluid volume and at a first fluid pressure;
    a valve system coupled between the fluid reservoir and the medical instrument;
    a vent;
    a flow sensor coupled between the valve system and the vent; and
    a control system including one or more processors, the control system configured to:
      activate the valve system to release a released fluid volume of the fluid from the fluid reservoir to the medical instrument;
      measure, with the flow sensor, a vented fluid volume through the vent; and
      determine a discharged fluid volume of fluid discharged through the medical instrument based on the released fluid volume and the vented fluid volume.

13. The system of claim 12 wherein activating the valve system includes opening the valve system for a duration of time calibrated to correspond with an expected discharge volume.

14. The system of claim 12 wherein the vented fluid volume passes through the valve system.

15. The system of claim 12 wherein the valve system includes at least two valves.

16. The system of claim 12 wherein the valve system includes a valve configured to act as a three-way valve.

17. The system of claim 12 further comprising a flow restrictor coupled between the fluid reservoir and the valve system, wherein the flow restrictor limits the released fluid volume.

18. The system of claim 12 wherein the control system is further configured to:

determine the released fluid volume based on the first fluid volume, the first fluid pressure, and a second fluid pressure in the fluid reservoir after the released fluid volume is released.

19. The system of claim 12 wherein the control system is further configured to:

determine if the discharged fluid volume exceeds or falls below a threshold.

20. The system of claim 19 wherein the control system is further configured to:

based on a determination that the discharged fluid volume exceeds the threshold, provide a warning indicator.

21. The system of claim 19 wherein the control system is further configured to:

based on a determination that the discharged fluid volume exceeds the threshold, prevent release of additional fluid volume from the fluid reservoir.

22. The system of claim 19 wherein the control system is further configured to:

responsive to a determination that an instrument has been moved in the medical instrument after release of the released fluid volume, release a second released fluid volume and determine a second discharged fluid volume.

23. The system of claim 12 wherein the medical instrument comprises a catheter.

* * * * *